(12) United States Patent
Tabata

(10) Patent No.: US 12,336,906 B2
(45) Date of Patent: Jun. 24, 2025

(54) ARTIFICIAL HEART VALVE

(71) Applicant: MITRAPEX, INC., Tokyo (JP)

(72) Inventor: Minoru Tabata, Tokyo (JP)

(73) Assignee: Mitrapex, Inc., Tokyo (JP)

( * ) Notice: Subject to any disclaimer, the term of this patent is extended or adjusted under 35 U.S.C. 154(b) by 900 days.

(21) Appl. No.: 17/403,889

(22) Filed: Aug. 17, 2021

(65) Prior Publication Data

US 2021/0369453 A1 Dec. 2, 2021

Related U.S. Application Data

(63) Continuation of application No. 16/486,501, filed as application No. PCT/JP2018/005444 on Feb. 16, 2018, now abandoned.

(30) Foreign Application Priority Data

Feb. 17, 2017 (JP) .................................. 2017-027391
Jun. 8, 2017 (JP) .................................. 2017-113165
Dec. 25, 2017 (JP) .................................. 2017-247166

(51) Int. Cl.
*A61F 2/24* (2006.01)

(52) U.S. Cl.
CPC .......... *A61F 2/2418* (2013.01); *A61F 2/2415* (2013.01); *A61F 2/2436* (2013.01); *A61F 2220/0008* (2013.01); *A61F 2220/0075* (2013.01)

(58) Field of Classification Search
CPC ........ A61F 2/24; A61F 2/2409; A61F 2/2415; A61F 2/2418; A61F 2/2412; A61F 2/2448; A61F 2/2445; A61F 2/2442; A61F 2/2457; A61F 2/246; A61F 2/2454; A61F 2/2463
See application file for complete search history.

(56) References Cited

U.S. PATENT DOCUMENTS

| | | | | |
|---|---|---|---|---|
| 4,790,844 | A * | 12/1988 | Ovil | A61F 2/2412 623/2.13 |
| 5,156,621 | A * | 10/1992 | Navia | A61F 2/2412 623/2.12 |
| 5,662,704 | A * | 9/1997 | Gross | A61F 2/2412 623/2.1 |
| 9,592,121 | B1 * | 3/2017 | Khairkhahan | A61B 17/064 |
| 10,080,659 | B1 * | 9/2018 | Zentgraf | A61F 2/2412 |
| 10,195,030 | B2 * | 2/2019 | Gross | A61F 2/2454 |
| 10,219,900 | B2 * | 3/2019 | Vidlund | A61F 2/2427 |
| 10,226,334 | B2 * | 3/2019 | Rowe | A61F 2/2436 |

(Continued)

FOREIGN PATENT DOCUMENTS

WO WO-2017061956 A1 * 4/2017 ............. A61B 34/10

*Primary Examiner* — Seema Mathew
(74) *Attorney, Agent, or Firm* — Pyprus Pte Ltd; George D. Liu

(57) ABSTRACT

To provide an artificial heart valve capable of aiding the functions of the mitral valve of a patient in a minimally invasive manner. An artificial heart valve 1 which includes a valve leaflet securing part 2 and valve leaflets (a first valve leaflet 5 and a second valve leaflet 7), and in which the valve leaflets are connected to the valve leaflet securing part 2 at the top portion of the artificial heart valve 1, the valve leaflets each have a region which narrows in width toward the bottom of the leaflet, and the artificial heart valve is an artificial mitral valve or an artificial tricuspid valve.

18 Claims, 8 Drawing Sheets

(56) References Cited

U.S. PATENT DOCUMENTS

| | | | |
|---|---|---|---|
| 10,226,335 B2* | 3/2019 | Cartledge | A61F 2/2418 |
| 10,265,172 B2* | 4/2019 | Krivoruchko | A61F 2/2457 |
| 10,278,814 B2* | 5/2019 | Scorsin | A61F 2/2412 |
| 10,405,976 B2* | 9/2019 | Christianson | A61F 2/2457 |
| 10,463,489 B2* | 11/2019 | Christianson | A61F 2/2439 |
| 10,470,877 B2* | 11/2019 | Tegels | A61F 2/2418 |
| 10,610,356 B2* | 4/2020 | Vidlund | A61F 2/2418 |
| 10,610,358 B2* | 4/2020 | Vidlund | A61F 2/2418 |
| 10,702,274 B2* | 7/2020 | Groothuis | A61B 17/0401 |
| 10,709,560 B2* | 7/2020 | Kofidis | A61F 2/2457 |
| 10,779,934 B2* | 9/2020 | Scorsin | A61F 2/2412 |
| 10,820,996 B2* | 11/2020 | Gifford, III | A61F 2/2454 |
| 10,952,844 B2* | 3/2021 | Vidlund | A61F 2/2418 |
| 10,952,852 B2* | 3/2021 | Barbarino | A61F 2/246 |
| 11,000,372 B2* | 5/2021 | Khairkhahan | A61F 2/2442 |
| 11,083,572 B2* | 8/2021 | McLean | A61F 2/2454 |
| 11,179,236 B2* | 11/2021 | Schankereli | A61F 2/2418 |
| 11,337,799 B2* | 5/2022 | Badhwar | A61F 2/24 |
| 11,464,634 B2* | 10/2022 | Khairkhahan | A61B 17/064 |
| 11,589,989 B2* | 2/2023 | Colli | A61F 2/2466 |
| 11,648,110 B2* | 5/2023 | Dale | A61F 2/2427 623/2.11 |
| 11,678,980 B2* | 6/2023 | Huddleston | A61F 2/2457 623/2.11 |
| 11,690,709 B2* | 7/2023 | Campbell | A61F 2/2448 623/2.38 |
| 11,911,266 B2* | 2/2024 | Rajagopal | A61F 2/2418 |
| 2001/0020189 A1* | 9/2001 | Taylor | A61F 2/02 623/23.68 |
| 2001/0020190 A1* | 9/2001 | Taylor | A61F 2/0004 623/23.68 |
| 2003/0078653 A1* | 4/2003 | Vesely | A61F 2/2457 623/23.72 |
| 2003/0199975 A1* | 10/2003 | Gabbay | A61F 2/2454 623/1.14 |
| 2004/0122513 A1* | 6/2004 | Navia | A61F 2/2412 623/2.12 |
| 2005/0075727 A1* | 4/2005 | Wheatley | A61F 2/2457 623/902 |
| 2005/0177180 A1* | 8/2005 | Kaganov | A61B 17/0057 606/151 |
| 2006/0178700 A1* | 8/2006 | Quinn | A61F 2/246 606/213 |
| 2006/0195182 A1* | 8/2006 | Navia | A61F 2/2412 623/2.16 |
| 2006/0195183 A1* | 8/2006 | Navia | A61F 2/2418 623/2.11 |
| 2006/0241745 A1* | 10/2006 | Solem | A61F 2/2442 623/2.18 |
| 2007/0093890 A1* | 4/2007 | Eliasen | A61F 2/246 623/2.11 |
| 2007/0265702 A1* | 11/2007 | Lattouf | A61B 17/0469 623/2.12 |
| 2007/0270943 A1* | 11/2007 | Solem | A61F 2/2466 606/151 |
| 2008/0027268 A1* | 1/2008 | Buckner | A61F 2/2448 600/16 |
| 2008/0086164 A1* | 4/2008 | Rowe | A61F 2/2466 606/191 |
| 2008/0228223 A1* | 9/2008 | Alkhatib | A61B 17/0401 606/221 |
| 2009/0012354 A1* | 1/2009 | Wood | A61F 2/2487 600/37 |
| 2009/0177274 A1* | 7/2009 | Scorsin | A61F 2/2457 623/2.1 |
| 2010/0023117 A1* | 1/2010 | Yoganathan | A61F 2/2457 623/2.37 |
| 2010/0023118 A1* | 1/2010 | Medlock | A61B 17/0487 606/228 |
| 2010/0179574 A1* | 7/2010 | Longoria | A61B 17/06166 606/151 |
| 2010/0280606 A1* | 11/2010 | Naor | A61F 2/2418 623/2.18 |
| 2012/0179244 A1* | 7/2012 | Schankereli | A61F 2/2418 623/2.11 |
| 2012/0197388 A1* | 8/2012 | Khairkhahan | A61B 17/064 623/2.11 |
| 2012/0226349 A1* | 9/2012 | Tuval | A61F 2/2409 623/2.37 |
| 2013/0023985 A1* | 1/2013 | Khairkhahan | A61L 27/06 623/2.38 |
| 2013/0079873 A1* | 3/2013 | Migliazza | A61F 2/2412 623/2.17 |
| 2014/0018906 A1* | 1/2014 | Rafiee | A61F 2/2427 623/1.26 |
| 2014/0031926 A1* | 1/2014 | Kudlik | A61F 2/2454 623/2.37 |
| 2014/0039607 A1* | 2/2014 | Kovach | A61B 17/0487 623/2.11 |
| 2014/0058503 A1* | 2/2014 | Umezu | A61B 17/32 623/2.15 |
| 2014/0163669 A1* | 6/2014 | Ben-Zvi | A61F 2/2418 623/2.11 |
| 2015/0094802 A1* | 4/2015 | Buchbinder | A61F 2/2454 623/2.38 |
| 2015/0100116 A1* | 4/2015 | Mohl | A61F 2/2454 623/2.11 |
| 2015/0112429 A1* | 4/2015 | Khairkhahan | A61B 17/064 623/2.11 |
| 2015/0119981 A1* | 4/2015 | Khairkhahan | A61F 2/2454 623/2.36 |
| 2015/0164637 A1* | 6/2015 | Khairkhahan | A61L 27/042 623/2.17 |
| 2015/0366666 A1* | 12/2015 | Khairkhahan | A61F 2/2466 623/2.11 |
| 2016/0030176 A1* | 2/2016 | Mohl | A61F 2/2454 623/2.11 |
| 2017/0172737 A1* | 6/2017 | Kuetting | A61F 2/2418 |
| 2017/0245994 A1* | 8/2017 | Khairkhahan | A61F 2/2457 |
| 2020/0214841 A1* | 7/2020 | Khairkhahan | A61B 17/0401 |
| 2022/0039951 A1* | 2/2022 | Khairkhahan | A61F 2/2466 |
| 2023/0293299 A1* | 9/2023 | Khairkhahan | A61F 2/2454 623/2.11 |
| 2024/0122701 A1* | 4/2024 | Sands | A61F 2/2418 |

* cited by examiner

ARTIFICIAL HEART VALVE

TECHNICAL FIELD

The present invention relates to an artificial heart valve. More specifically, the present invention relates to an artificial heart valve for medical use provided in the vicinity of mitral valve or in the vicinity of the tricuspid valve to assist the function of the mitral valve or the tricuspid valve.

BACKGROUND TECHNOLOGY

Mitral valve regurgitation or inefficiency is a disease in which closing function of the mitral valve is impaired so that a portion of blood ejected from the left ventricle into the aorta is caused to flow in backward direction into the left atrium. For example, the functional mitral regurgitation (FMR), which is one of the mitral valve inefficiencies, is a disease in which blood regurgitation takes place due to impaired function or deformation of the left ventricle or the left atrium, etc. although the mitral valve itself is normal.

In, e.g., the Japanese Patent No. 5392539 publication, stainless artificial mitral valve and artificial heart valve leaflets are described for the purpose of treating mitral valve regurgitation. This artificial mitral valve is sutured to the annulus of the heart (paragraph [0032] of this document). Namely, this artificial mitral valve is a surgically implanted artificial mitral valve, and it is implanted with opening the chest and using a cardiopulmonary bypass machine. Such open heart surgery is a large burden on the patient, and usually requires a long time until recovery.

On the other hand, in US Patent No. 2012-179244's specification, an artificial mitral valve using a stent is described. Such artificial mitral valve using transcatheter approach and a stent is less invasive as compared to surgically implanted artificial mitral valve. On one hand, with stented artificial mitral valve described in this publication, the mitral valve of the patient himself becomes unfunctional although native mitral valve itself with functional mitral valve regurgitation (FMR) is normal. On the contrary, mitral valve of patients in which such stented artificial mitral valve is implanted is a nuisance, and can obstruct the left ventricular outflow tract.

The tricuspid valve is a valve located between the right atrium and the right ventricle of the heart. The tricuspid valve has a function to prevent backflow of blood. In regard to such tricuspid valve, there is a disease such as tricuspid valve inefficiency (tricuspid regurgitation)

In JP-A 2016-28762, an artificial heart valve (artificial mitral valve or artificial tricuspid valve) using a stent is described. Also with respect to such artificial heart valve, native heart valve itself becomes unfunctional. For this reason, when such artificial valve using a stent is implanted, the interaction with the left ventricular contraction that the original mitral valve has may be lost, leading to lowering in the cardiac function.

PRIOR ART

Patent Document

Patent Document 1: Japanese Patent No. 5392539 publication
Patent Document 2: U.S. Patent 2012-179244 specification
Patent Document 3: JP A2016-28762

SUMMARY OF THE INVENTION

Problems that the Invention Intends to Solve

The present invention has an object to provide an artificial heart valve which is capable of assisting, in a minimally invasive manner, the function of the mitral valve and/or the tricuspid valve of patients.

Means for Solving the Problems

The present invention relates to an artificial valve 1 (artificial heart valve) comprising a ring 3, a first valve leaflet 5, and a second valve leaflet 7.

The first valve leaflet 5 and the second valve leaflet 7 are connected to the ring 3 at an upper part of the artificial valve 1.

The first valve leaflet 5 and the second valve leaflet 7 are connected to a lower part junction 9 existing at a lower part of the artificial valve 1.

The first valve leaflet 5 and the second valve leaflet 7 have, at a lower part of the ring 3, portions which become narrower in width toward the bottom thereof. Further, it is preferable that the valve leaflet has a shape which is narrowest in width at the lower end thereof.

This artificial valve functions as an artificial valve which assists the function of the mitral valve or the tricuspid valve.

It is preferable that this artificial valve is preferably such that an upper part of the first valve leaflet 5 and an upper part of the second valve leaflet 7 are connected at an upper part junction 11.

This artificial valve is preferably such that when the circumference of the ring 3 is assumed to be 100%, the first valve leaflet 5 or the second valve leaflet 7 is connected at portions of 30% to 99% both inclusive of the circumference of the ring 3.

This artificial valve is preferably such that the ring 3 can be folded, and can be opened within the left atrium or the right atrium.

It is preferable that the ring has an annular shape having a diameter of 30 mm to 60 mm both inclusive.

It is preferable that either of the ring 3, the first valve leaflet 5 and the second valve leaflet 7 has an anchoring portion 13 for anchoring it to the left atrial wall or the right atrial wall. The anchoring portion 13 may be adapted to be held to the right atrial wall.

This artificial valve may be preferably such that the anchoring portion 13 is an adhering portion or portions to the left atrial wall or the right atrial wall, which is or are provided at either one of the first valve leaflet 5 and the second valve leaflet 7 or at the both valve leaflets. The anchoring portion 13 may be an adhering portion to the right atrial wall.

The above-mentioned problems can be also solved by an artificial heart valve described below. This artificial heart valve is an artificial heart valve 1 comprises a valve leaflet securing part 2, and at least one valve leaflet 4. The artificial heart valve is an artificial mitral valve or an artificial tricuspid valve. The valve leaflet 4 is connected to the valve leaflet securing part 2 at an upper part of the artificial heart valve 1. An example of the valve leaflet securing part 2 is ring 3 or securing end (band) 6, 8. The valve leaflet 4 has a portion 37 which becomes narrower in width toward the bottom thereof. The combination of the type of artificial heart valves and the valve leaflet securing part 2 may be arbitrary. For example, the artificial valve may be artificial mitral valve, the valve leaflet securing part 2 may be ring 3, and any other combination except therefor may be adopted. The artificial heart valve may comprise means for preventing the artificial mitral valve or the artificial tricuspid valve from passing therethrough. An example of the passage preventing means may be an anchoring portion which will be described later.

The valve leaflet securing part 2 is (i) a ring 3, or (ii) a securing end 6, 8 attached to the valve leaflet 4.

Another embodiment different from the above-mentioned artificial heart valve which can solve the above-mentioned problems is an artificial heart valve 1 comprising valve leaflet securing part 2, first valve leaflet 5 and second valve leaflet 7.

The first valve leaflet 5 and the second valve leaflet 7 are connected to the valve securing part 2 at an upper part of the artificial heart valve 1.

The first valve leaflet 5 and the second valve leaflet 7 are connected at a lower part junction 9 existing at a lower part of the artificial heart valve 1.

The first valve leaflet 5 and the second valve leaflet 7 have portions which become narrower in width toward the bottom thereof.

Moreover, the first valve leaflet 5 and the second valve leaflet 7 may have a shape which is the narrowest in width at the lower part junction 9 or below the lower part junction 9.

The artificial heart valve is the artificial mitral valve or the artificial tricuspid valve. More specifically, an example of the valve leaflet securing part 2 is ring 3, first securing end 6 and second securing end 7. The combination of the type of artificial heart valves and the valve leaflet securing part 2 are arbitrary. For example, the artificial heart valve may be an artificial mitral valve, and the valve securing part 2 may be ring 3, and combinations except therefor may be adopted.

A preferred example of the artificial heart valve comprises an apical junction 10 in contact with the ventricular apex (of the right ventricle or the left ventricle) at the lower part junction 9 or below the lower part junction 9.

The valve leaflet securing part 2 is (i) a ring 3, or (ii) a first securing end 6 and a second securing end 7 which are respectively attached to the upper part of the first valve leaflet 5 and the upper part of the second valve leaflet 7. The first securing portion 6 and the second securing portion 7 may be respectively curved, or may be respectively straight. Further, the first securing end 6 and the second securing end 7 may be respectively changeable in shape (flexible).

Either one of the valve leaflet securing part 2, the first valve leaflet 5 and the second valve leaflet 7 may comprise an anchoring portion 13 for anchoring it to the atrial wall. The anchoring portion 13 may be an adhering portion or portions to the atrial wall, which is or are provided at either one of the first valve leaflet 5 and the second valve leaflet 7 or at the both valve leaflets.

The anchoring portion may be held or adhere to the atrial wall or the atrioventricular valve annulus.

In addition, either valve leaflet (in the case of an artificial heart valve having a single valve leaflet, that valve leaflet, and in the case of an artificial heart valve having two valve leaflets, single or two valve leaflets) may further comprise a securing part 75 for connecting the valve leaflet and a ventricular wall or a papillary muscles.

Effects and Advantages with the Invention

The present invention can provide an artificial heart valve capable of assisting, in a minimally invasive manner, the function of the mitral valve or the tricuspid valve of patient.

BEST MODE FOR CARRYING OUT THE INVENTION

Preferred embodiments for carrying out the present invention will now be described with reference to the attached drawings. It should be noted that the present invention is not limited to embodiments as described below, but comprises an embodiment or embodiments that those persons skilled in the art have modified as occasion demands within a self-explanatory range from such embodiment or embodiments.

Figure 1:
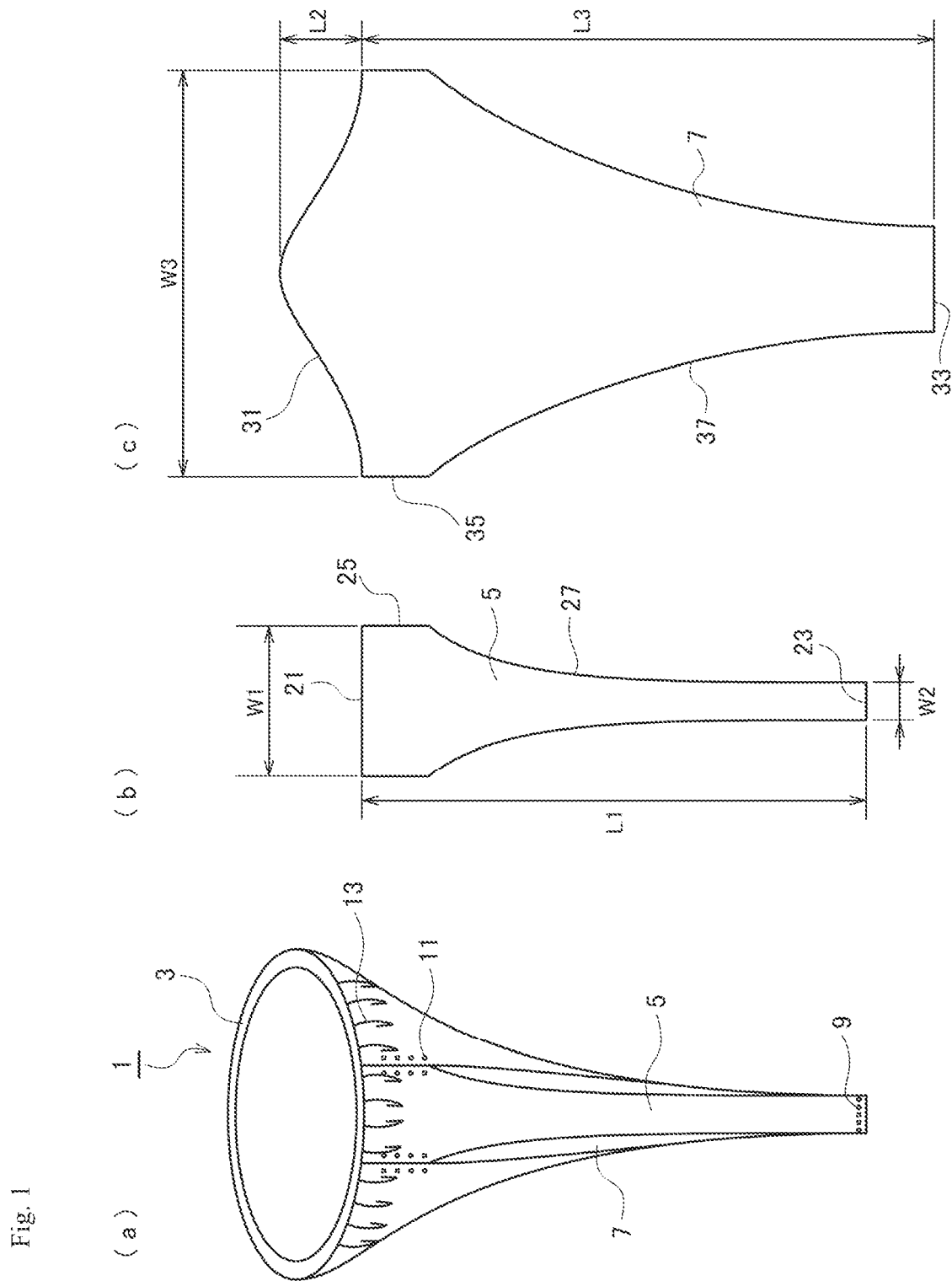
FIG. 1 is a conceptual diagram illustrating an example of an artificial heart valve according to the present invention.

FIG. 1 is a conceptual diagram illustrating an example of an artificial heart valve according to the present invention. FIG. 1(*a*) illustrates an outside diagram. FIG. 1(*b*) illustrates a conceptual diagram of a first valve leaflet. FIG. 1(*c*) illustrates a conceptual diagram of a second valve leaflet. An example illustrated in FIG. 1 is such that the valve leaflet securing portion 2 is ring 3, and is used for the mitral valve. The valve leaflet securing portion 2 is secured to the valve leaflets so as to permit the first valve leaflet and the second valve leaflet to continuously locate above the heart valve (within the atria). Moreover, the valve leaflet securing part 2 may be continuously disposed suitably within the atria as the result that it is connected to the atrial wall. For example, since the ring has a diameter larger than that of the heart valve, the situation where it moves toward ventricular side can be prevented.

The artificial heart valve 1 according to the present invention illustrated in FIG. 1 comprises the ring 3, the first valve leaflet 5, and the second valve leaflet 7. The first valve leaflet 5 and the second valve leaflet 7 may have the same shape, or may have shapes different from each other. Further, the first valve leaflet 5 and the second valve leaflet 7 are connected to the ring 3 at the upper part of the artificial heart valve 1. The first valve leaflet 5 and the second valve leaflet 7 may be such that the upper end or the region in the vicinity of the upper end (e.g., the region of 0.1 mm to 10 mm both inclusive from the upper end) may be sewn to the ring 3. The first valve leaflet 5 and the second valve leaflet 7 are connected at a lower part junction 9 of the artificial heart valve existing at the lower part of the artificial heart valve 1. Moreover, the first valve leaflet 5 and the second valve leaflet 7 have shape portions which become narrower in width toward the bottom thereof. The lower part junction 9 may be lower ends of the first valve leaflet 5 and the second valve leaflet 7, or may be located within the region in the vicinity of the lower end (e.g., the region which is of 0.1 mm to 10 mm both inclusive from the lower end). Further, the first valve leaflet 5 and the second valve leaflet 7 may have a shape which is the narrowest in width at the lower end. Further, the first valve leaflet 5 and the second valve leaflet 7 have a shape which is the narrowest in width at the lower end thereof. Further, the first valve leaflet 5 and the second valve leaflet 7 may be broader in width than that of the lower part junction 9 at their lower ends thereof. In addition, it is preferable that either one of the first valve leaflet 5 and the second valve leaflet 7 or the both valve leaflets has or have a shape which is the narrowest in width at the lower end or ends thereof.

The ring 3 has an annular shape having a diameter, e.g., of 30 mm to 60 mm both inclusive (or 35 mm to 55 mm both inclusive, 40 mm to 50 mm both inclusive). The ring 3 may have an elliptical shape or a circular shape so as to adapt to the shape of the left atrium (or the right atrium). It is preferable that the ring 3 is manufactured by bio-adaptive material. The ring may comprise metal (spring) so that it can be folded and can be deployed, or may be resin material. An example of the ring made of resin is a ring made of silicon as the resin.

An example of the thickness (diameter) of the ring is 1 mm to 20 mm both inclusive, and may be 5 mm to 15 mm both inclusive, may be 1 mm to 5 mm both inclusive, and may be 8 mm to 12 mm both inclusive. Particularly, in the case of an artificial heart valve comprising a single valve leaflet, it is preferable to employ a ring having a relatively larger thickness.

For the first valve leaflet 5 and the second valve leaflet 7, known materials used in the artificial heart valve may be used. An example of materials for the valve leaflet is membrane derived from human stem cells, and tissue derived from mammals (e.g., pigs, cows, horses). As another example of material for valve cusp, tissue derived from the patient may be used. As tissue derived from the patient, there may be adopted a tissue reproduced by using bio-tissue material collected from the patient. The bio-tissue substance is a substance necessary for forming bio-derived material. An example of the bio-tissue material is fibroblasts, smoothing muscle cells, endothelial cells, stem cells, animal cells such as ES cells and/or iPS cells, etc., various kinds of proteins (collagen, elastin), saccharides such as hyaluronic acid, etc., cell growth factors, and cytokine. By placing base material for forming artificial heart valve under the environment where bio-tissue substance exists, it is possible to form processable connective tissue body on the surface of the base material for forming the artificial heart valve. Another example of material for the valve leaflet is resin or plastics.

This artificial heart valve has a shape such that the lower ends of the first valve leaflet 5 and the second valve leaflet 7 are narrow in width. For this reason, this artificial heart valve is inserted from the left ventricle (or the right ventricle) to open the ring at the left atrium (or the right atrium) thereafter to permit the lower ends of the first valve leaflet 5 and the second valve leaflet 7 to be implanted into the portion of the left ventricle or the left ventricular apex 53 into which the artificial heart valve has been inserted. Therefore, this artificial heart valve will be stable within the heart of patients. Namely, it is preferable that the artificial heart valve according to the present invention has a size such that the end portion of the artificial heart valve arrives at the left ventricular apex, or a length in which it is beyond the left ventricular apex when the ring is located within the left atrium (or the right atrium). Namely, this artificial heart valve is preferably an artificial heart valve for assisting the mitral valve, and is an artificial heart valve in which the ring stays within the left atrium (or the right atrium), and the lower part of the valve leaflet of the artificial heart valve arrives at the left ventricular apex to secure the lower end of the valve leaflet of the artificial heart valve is secured to the left ventricular apex after the length of the artificial heart valve is adjusted.

It is preferable that, when connected to the valve leaflet securing part 2 as the artificial heart valve, these valve leaflets 5 and 7 have shapes in which the portion in contact with the valve leaflet securing part 2 is the broadest in width, and which is unchanged in width toward the bottom thereof from the portion in contact with the valve leaflet securing part 2, or which becomes narrower in width toward the bottom thereof. To the contrary, these valve leaflets 5 and 7 may have a shape comprising a portion which is gently swollen in width on the way toward the bottom thereof. Even in the case of valve leaflets 5 and 7 having a shape which becomes broader in width on the way, it is preferable that those valve leaflets have a width which is narrower than that of the portion in contact with the valve leaflet securing part 2. It is preferable that the first valve leaflet 5 and the second valve leaflet 7 are connected at least at the lower part junction 9. It is preferable that the lower part junction 9 is provided at the lower part of the valve leaflet.

The first valve leaflet 5 illustrated in FIG. 1(b) will now be described. This valve leaflet is such that width W1 of an upper end 21 which is a portion sewn to the ring 3 is, for example, 30 mm to 90 mm both inclusive. The width W1 may be 40 mm to 80 mm both inclusive, and may be 45 mm to 70 mm both inclusive. The first valve leaflet is preferably such that when the circumference of the ring 3 is assumed to be 100%, the portion of 15% to 45% both inclusive of the circumference of the ring is coated (or is connected at that portion), and may be such that the portion of 20% to 40% both inclusive is coated and may be such that the portion of 20% to 30% both inclusive is coated. The valve leaflet 5 illustrated in FIG. 1(b) is such that a portion uniform in width exists on the upper portion thereof. This portion is a junction 25 to the second valve leaflet 2. An example of the length (height) of this portion 25 is 1 mm to 10 mm both inclusive, and may be 2 mm to 8 mm both inclusive, and may be 4 mm to is 8 mm both inclusive. In this example, there exists a portion 27 which becomes narrower in width in a curved manner from the upper part constant in width toward the lower end 23. An example of the width of the lower end 23 is 2 mm to 20 mm both inclusive, and may be 3 mm to 10 mm both inclusive, and may be 3 mm to 5 mm both inclusive. The height L1 of the first valve leaflet 5 is 20 mm to 70 mm both inclusive, and may be 25 mm to 65 mm both inclusive, may be 30 mm to 40 mm both inclusive, may be 40 mm to 70 mm both inclusive, and may be 40 mm to 60 mm both inclusive. The concrete size of the valve leaflet may be designed by taking into account, e.g., the shape of the heart of patients, the degree of blood regurgitation and the state of disease. The shape portion which becomes narrower in width toward the bottom thereof may be equal to the entirety of the height L1 of the first valve leaflet 5, and may be 30% to 100% both inclusive, may be 50% to 100% both inclusive, may be 70% to 100% both inclusive, may be 80% to 100% both inclusive, and may be 90% to 100% both inclusive. The upper limit of the shape portion which becomes narrower in width toward the bottom may be 99%, 98%, 97%, 95%, 91% in place of 100%. Moreover, the valve leaflet may have, e.g., a shape which is not changed in width from the upper end of the valve leaflet until the middle way thereof, or becomes narrower in width toward the bottom thereof. Further, the valve leaflet may have a shape which is not changed in width from the upper end thereof until the middle way thereof, or becomes narrower in width toward the bottom thereof, and further has a portion which becomes broader in width at the lower end portion thereof. The shape portion which becomes narrower in width toward the bottom thereof also similarly applies to other valve leaflets in this specification.

The second valve leaflet 7 illustrated in FIG. 1(c) may be manufactured fundamentally in a manner similar to the first valve leaflet 5. On one hand, the second valve leaflet may be thicker than the first valve leaflet. By doing so, a difference in rigidity between these valve leaflets will generate, thus making it possible to effectively prevent blood regurgitation. When the average thickness of the first valve leaflet is designated at $d_1$, and the thickness of the second valve leaflet is designated at $d_2$, $d_1$ and $d_2$ may be equal to each other. On the other hand, when thicknesses of these two valve leaflets are different from each other, there may hold $1.01\ d_1 \leq d_2 \leq 3\ d_1$, there may hold $1.05\ d_1 \leq d_2 \leq 2.5\ d_1$, there may hold $1.5\ d_1 \leq d_2 \leq 2.5\ d_1$, and there may hold $1.75\ d_1 \leq d_2 \leq 2.5\ d_1$. L3 illustrated in FIG. 1(c) may be to the same degree as that of L1 in FIG. 1(b). Moreover, the lower end 33 of the second valve leaflet may be a width to the same degree as that of the lower end 23 of the first valve leaflet. The upper part 31 of the second valve leaflet is such that a gentle convex part (projected part) 31 exists in a manner to fit the shape of the ring. Further, a junction 35 which is a portion constant in width exists at the upper part of the second valve leaflet. This portion may be sutured into the connecting portion 25 of the first valve leaflet. In this example, there exists a portion 37 which becomes narrower in width in a curved manner from the upper part which is constant in width toward the lower end 33.

This artificial heart valve may be such that the upper part of the first valve leaflet 5 and the upper part of the second valve leaflet 7 are connected at the upper part junction 11 of the artificial heart valve 1. In that case, since those two valve leaflets are connected, the stability of the valve leaflets will be enhanced. Further, this artificial heart valve is such that the lower portions of the first valve leaflets and the second valve leaflets are connected at the lower part junction 9. Thus, the portion between these junctions can be swollen or contracted. By such operation, this artificial heart valve can prevent blood regurgitation.

It is preferable that this artificial heart valve is such that the ring 3 can be folded and can be opened within the left atrium (or the right atrium). When this artificial heart valve has such property, it can be inserted into the heart and can be placed there within in a transcatheter manner. For this reason, the open heart surgery becomes unnecessary in order to place the artificial heart valve.

Also for the ring 3, it is preferable to employ a ring with such a supporting rod (or thread like member) to connect ends of the circle. The supporting rod may be formed by means of thread bridging over the diameter or the edge portions of the ring. Provision of such a supporting rod can maintain the shape of the ring, thus to effectively prevent the situation in which the valve leaflet deviates toward the atrial side.

This artificial heart valve is preferably such that either one of the ring 3, the first valve leaflet 5 and the second valve leaflet 7 is provided with an anchoring portion 13 for anchoring it to the left atrial wall (or the right atrial wall). The anchoring portion 13 may be an adhering portion to the left atrial wall (or the right atrial wall) provided at either one of the first valve leaflet 5 and the second valve leaflet 7 or at the both valve leaflets. Since such anchoring portion 13 is provided, there is no necessity for such artificial heart valve to secure to the left atrium (or the right atrium) by suturing.

The anchoring portion may be held or adhere to the atrial wall or the atrioventricular valve annulus. The anchoring method is similar to the above. An example of the anchoring method may provide sewing to a tissue to be held, and/or may biologically adhere (tissues or tissue and element adhere to each other). The valve annulus generally refers to the root portion of the valve. The atrioventricular valve refers to either one of the mitral valve and the tricuspid valve, or both valves.

An example of the anchoring portion 13 as illustrated in FIG. 1 is a plurality of hooks provided at the outer circumference of the ring 3. This hook is hooked to the left atrium (or the right atrium), thus preventing the ring 3 from being fluctuated within the left atrium (or the right atrium). The anchoring portion 13 may be a plurality of very small projections provided on the ring 3. Since too large projections damages the atrium, an example of the length (height) of the projection is 0.1 mm to 5 mm both inclusive, and may be 0.2 mm to 3 mm both inclusive, and may be 0.2 mm to 1 mm both inclusive. Such projections may be manufactured by any biocompatible substance. Such projections may comprise a coating layer on the surface thereof. The coating layer may comprise, e.g., trehalose and various chemicals. Moreover, the coating layer may comprise any substance which secretes adhering substance such as fibrin, etc. or adhering substance in-vivo so that the ring or the valve leaflet upper part and the left atrium (or the right atrium) adhere to each other. When the first valve leaflet 5 or the second valve leaflet 7 comprises an adhering portion, the valve leaflet may comprise, e.g., a plurality of uneven portions or a plurality of projections provided, e.g., at the upper portion thereof (e.g., a region within 20 mm from a portion connected to the ring 3, or a region within 15 mm therefrom). In addition, such valve leaflet may comprise an adhesion induced layer which is manufactured by adhering material is applied on the upper part of the valve leaflet.

Another example of the anchoring portion 13 is a fold provided at the outer circumference of the ring. When this fold is viewed from the upper surface, for example, it has an annular shape, wherein the inner circumferential portion of this fold is connected to the ring. This fold has a shape in which a portion having a shape of a triangular wave comprising mountain portions and valley portions which are continuous to each other surrounds the inner circumferential portion. The width of the annular portion may be adjusted as occasion demands, and may be 0.1 mm to 20 mm both inclusive, may be 0.5 mm to 10 mm both inclusive, and may be 1 mm to 5 mm both inclusive.

Figure 2:
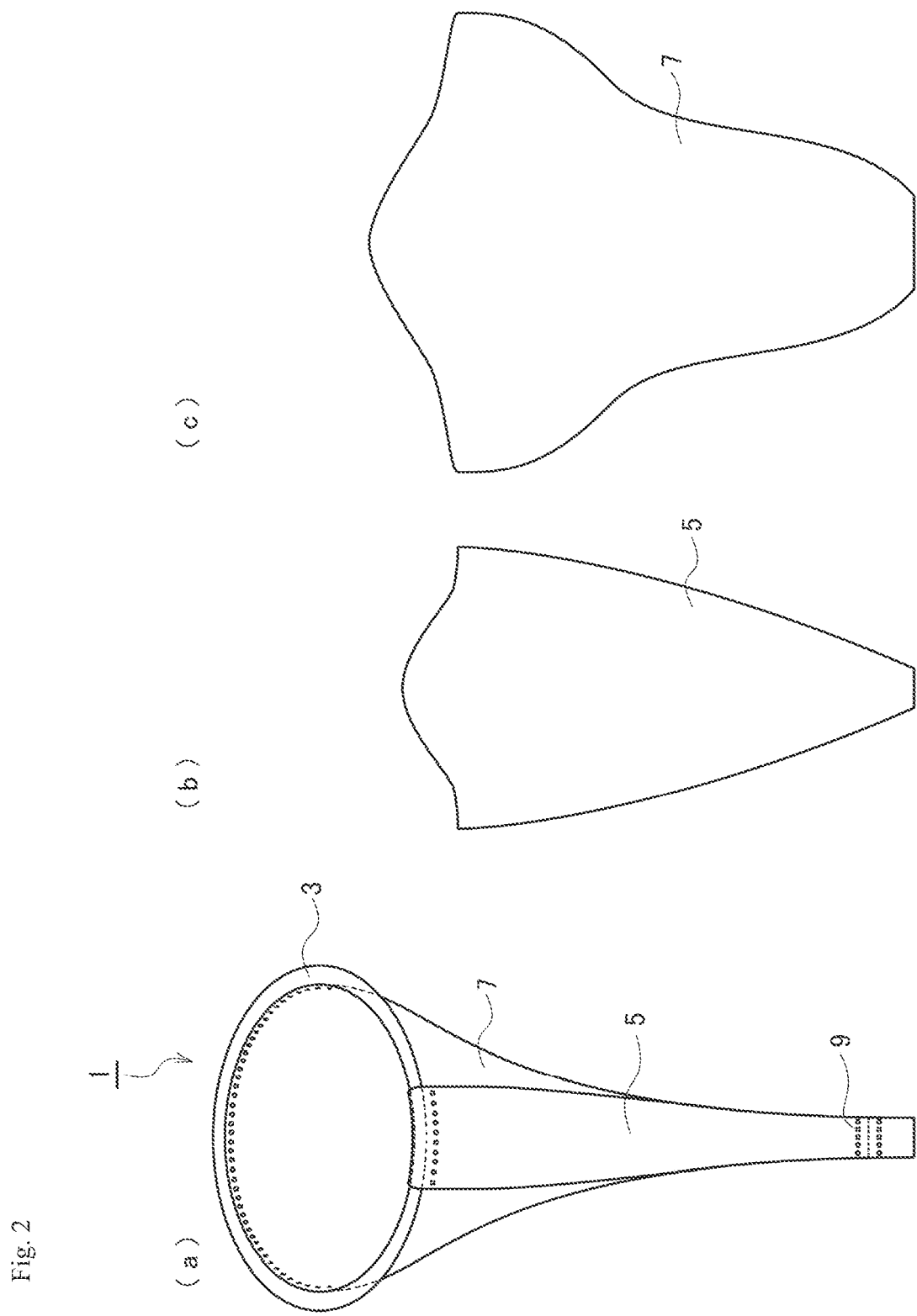
FIG. 2 is a conceptual diagram illustrating an example of an artificial heart valve according to the present invention.

FIG. 2 is a conceptual diagram illustrating an example of the artificial heart valve according to the present invention. FIG. 2(a) illustrates an outside diagram. FIG. 2(b) illustrates a conceptual diagram of the first valve leaflet. FIG. 2(c) illustrates a conceptual diagram of the second valve leaflet. As illustrated in FIG. 2, the artificial heart valve according to the present invention is not required to cover the ring with the first and second valve leaflets. In the artificial heart valve, the region where the first valve leaflet 5 and the second valve leaflet 7 are connected to the ring 3 may be a region of 30% to 99% both inclusive (or a region 35% to 90% both inclusive) of the ring 3. The artificial heart valve of the above-mentioned patent document 1 (the Japanese Patent No. 5392539 publication) is adapted so that the region which is about one half of the ring is covered with two valve leaflets. In this example, as illustrated in FIG. 2(a), when assembled as an artificial heart valve, any portion which is constant in width does not exist in the first valve leaflet (FIG. 2(b)) and the second valve leaflet (FIG. 2(c)), although their widths become narrower from the upper end toward the lower end with respect to the portion to be connected to the ring 3, a plurality of inflection points exist in that curve. Namely, as the shape of the valve leaflet, there may be adopted not only valve leaflets which uniformly become narrower, but also valve leaflets which become broader on the way toward the lower end and valve leaflets which are remarkably uneven.

Figure 3:
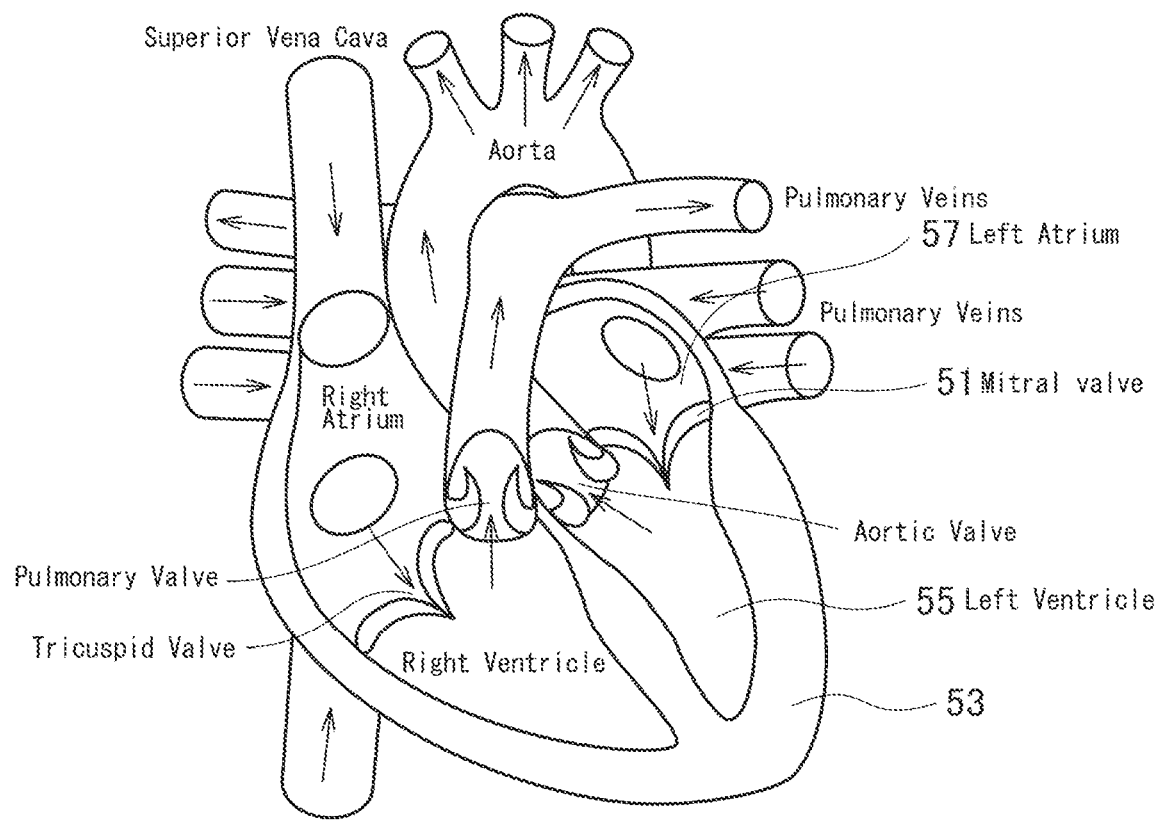
FIG. 3 is a conceptual diagram for explaining organs around the heart.

An example of a method of manufacturing an artificial heart valve according to the present invention will now be described. FIG. 3 is a conceptual diagram for explaining organs around the heart. Arrows in the figure indicate directions of blood flow. The artificial valve heart according to the present invention serves to fundamentally assist the function of the mitral valve 51. First of all, information such as sizes of a heart of the patient, the state of muscle 53 constituting the left ventricle, the shapes of the left ventricle 55 and the left atrium 57, and/or the stage of the mitral valve blood regurgitation (the function of the mitral valve) are collected. Further, when it is determined to use the artificial heart valve according to the present invention, the material and the sizes of the artificial heart valve are then determined. A reproductive medicine is performed in dependency upon the material of the membrane of the valve leaflet thus to provide a material for the membrane. The valve leaflet is then cut out from the membrane. Thereafter, processing is implemented to the valve leaflet as occasion demands. Further, the upper part of the valve leaflet is sewn to the ring. On the other hand, the lower portions of the valve leaflet are sewn to each other. In this way, an artificial heart valve is provided. This example is an example of a method of manufacturing the artificial heart valve, and e.g., artificial heart valves or valve membranes of several sizes may be prepared in advance to assemble them in correspondence with patients.

Figure 4:
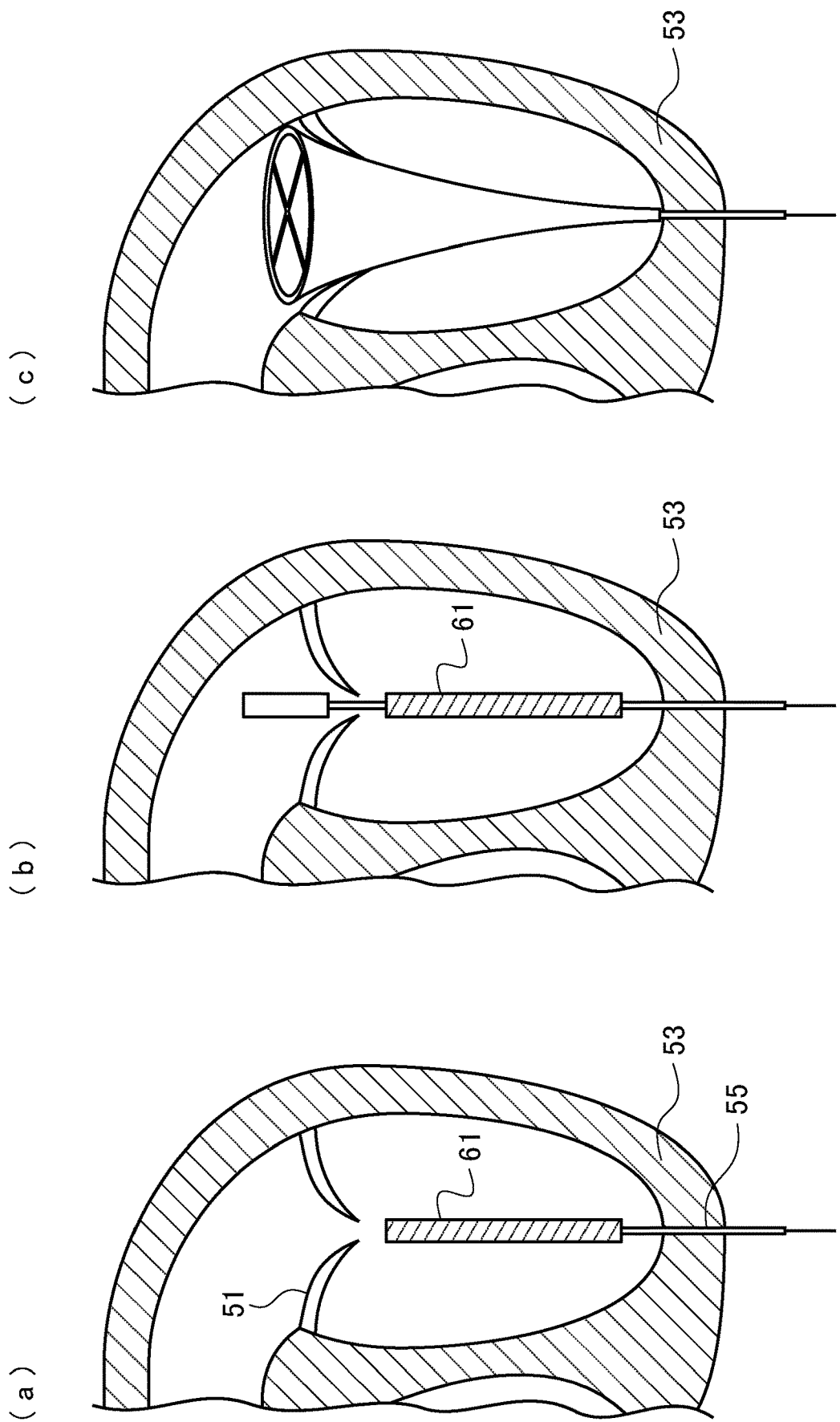
FIG. 4 is a conceptual diagram illustrating a use example of the artificial heart valve according to the present invention.

FIG. 4 is a conceptual diagram illustrating a use example of the artificial heart valve according to the present invention. In this example, the left small thoracotomy approach is performed under the general anesthesia. The artificial heart valve is contained into a sheath (container) 61 in the folded state, and is conveyed to a portion in the vicinity of the left ventricle through blood vessel. Further, the sheath 61 is penetrated through the left ventricular apex 53, and is passed between the anterior valve leaflet and the posterior valve leaflet of the mitral valve through the left ventricle 55, whereby such sheath is reached into the left atrium. In the state where the artificial heart valve exists within the left atrium, the sheath 61 is withdrawn therefrom. Thus, the ring is deployed within the left atrium. Thereafter, the alignment between the mitral valve of the patient and the artificial heart valve is made by using the echo-guide, and the anchoring portion (hook) 13 is secured to the left atrial wall. The lower end of the artificial heart valve is caused to be situated outside of the left ventricular apex 53, and the length of the artificial heart valve is adjusted while observing the junction of the artificial heart valve by means of echo. After the length is determined in this way, the valve leaflet is secured to the left ventricular apex 53. The artificial heart valve is thus placed so as to overlie the patient's own valve. By doing so, the patient's own valve of the patient will be also activated in a manner as before. In addition, the continuity to the left ventricular wall is maintained in both the patient's own valve and the artificial heart valve.

Also in this example, it is preferable that the artificial heart valve is in contact with or is secured to the valve cusp of the left ventricle. For example, by securing the end of the artificial heart valve by means of clip, etc. at the outside of the left ventricle, it is possible to maintain the shape of the artificial heart valve within the heart.

An artificial heart valve comprising the valve leaflet securing portion 2 as the ring 3, and used for tricuspid valve will now be described. An artificial heart valve for tricuspid valve may be adjusted as occasion demands in correspondence with sizes of the valve and also be prepared in a manner similar to the artificial heart valve for mitral valve, and the ring 3 may be placed within the atrium, further the lower part of the valve leaflet is placed within the left ventricle. It is to be noted that the artificial heart valve according to the present invention assists the function of the tricuspid valve and is effective for treatment of the tricuspid valve regurgitation.

The case where the valve leaflet securing part 2 is a first securing end 6 and a second securing end 8 which are respectively attached to the upper part of the first valve leaflet 5 and the upper part of the second valve leaflet 7 will now be described.

Figure 5:
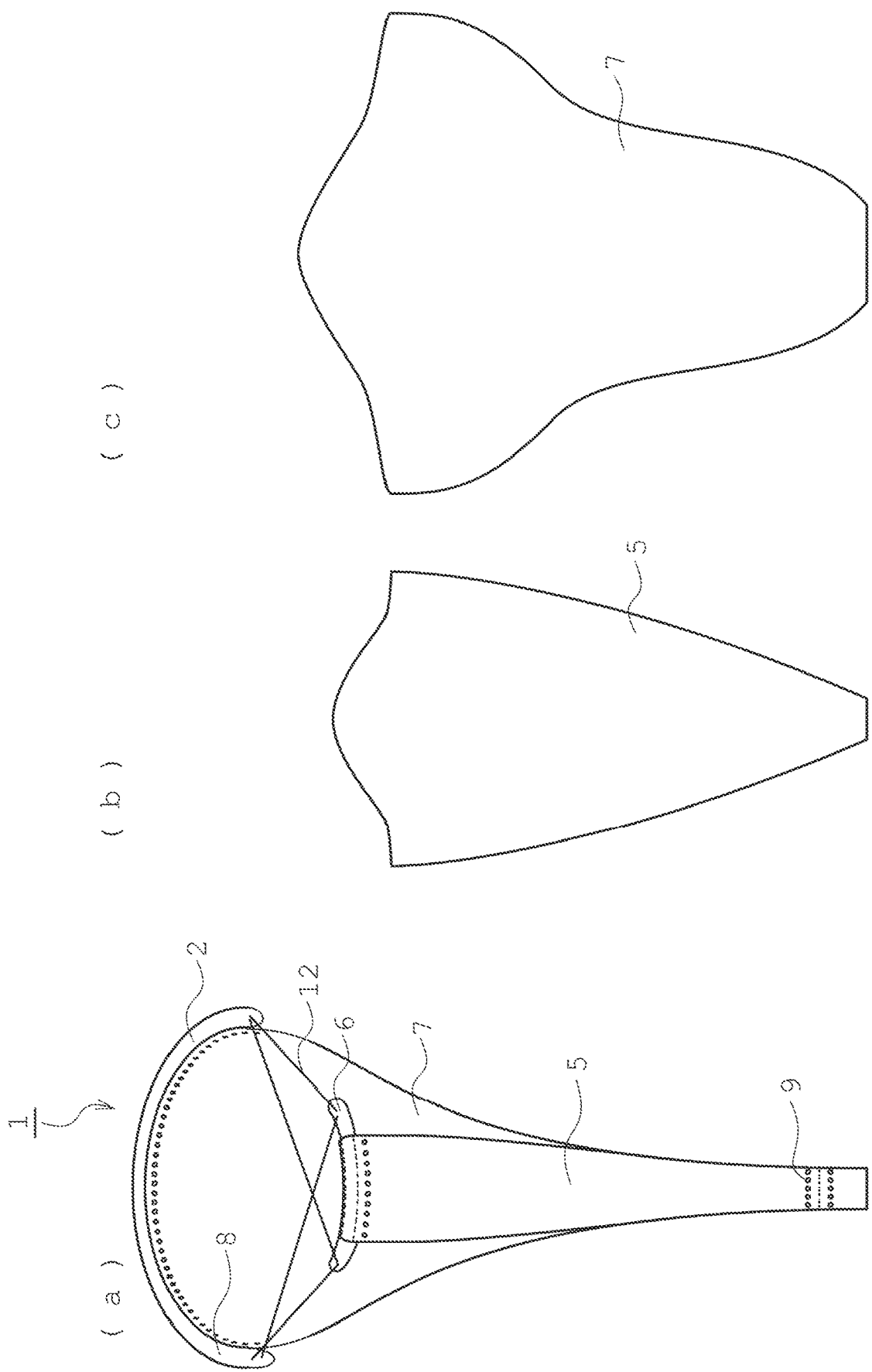
FIG. 5 is a conceptual diagram illustrating an example of an artificial heart valve according to the present invention having a securing end.

The valve leaflet securing part 2 is an element for preventing the valve leaflet upper portion existing within the atrium from moving into the ventricle. Ordinarily, the valve leaflet securing part 2 is larger than (e.g., longer than) the space of the cardiac valve (mitral valve, or tricuspid valve). FIG. 5 is a diagram illustrating an example of an artificial heart valve having a securing end. The securing portions 6 and 8 serving as the first and second securing ends 6 and 8, which are respectively attached to the upper portion of the first valve leaflet 5 and the upper portion of the second valve leaflet 7, may be a rod in which the curved shape is approximately constant, or a straight rod. In spite of these shapes, it is preferable that the securing ends 6, 8 have a hardness higher than the valve leaflets 5, 7. An example of the lengths of these securing ends 6, 8 are 10 mm to 90 mm both inclusive. The lengths of these securing ends 6, 8 may be 20 mm to less than 90 mm, may be larger than 40 mm and less than 80 mm, and may be 45 mm to 70 mm both inclusive. It is preferable that the first securing end 6 and the second securing end 8 respectively have lengths of the upper part of the valve leaflet 5 and the upper part of the second valve leaflet 7, or respectively have lengths longer than the upper part of the first valve leaflet 5 and the upper part of the second valve leaflet 7.

An example of the thickness (maximum diameter) of the securing end is 1 mm to 20 mm both inclusive, and may be 5 mm to 15 mm both inclusive, may be 1 mm to 5 mm both inclusive, and may be 8 mm to 12 mm both inclusive. Particularly in the case of a single valve leaflet, a valve leaflet having a relatively thick securing end is preferable. In addition, the securing end may be provided with the above-mentioned anchoring portion.

FIG. 5 is a conceptual diagram illustrating an example of an artificial heart valve according to the present invention having a securing end. FIG. 5(a) illustrates an outside diagram of the artificial heart valve. FIG. 5(b) illustrates a conceptual diagram of the first valve leaflet. FIG. 2(c) illustrates a conceptual diagram of the second valve leaflet. In the example illustrated in FIG. 5, first securing end 6 is attached on the upper part of the first valve leaflet 5. On one hand, a second securing end 8 is provided on the upper part of the second valve leaflet 7. In the example illustrated in FIG. 5, it is preferable that those securing ends 6 and 8 of the artificial heart valve are larger (longer) than the space within the valve that the artificial heart valve forms so that these securing ends 6, 8 are stably located within the atrium, and are not moved into the ventricles. Nevertheless, these securing ends 6, 8 are preferably secured to the left atrial wall or the right atrial wall by means of the anchoring portion. For this reason, the lengths of the securing ends 6, 8 may be shorter than the valve port. The anchoring portion may employ, as occasion demands, the anchoring portion which has been previously described, and may be such that these securing ends 6, 8 are cased to adhere to the atrial wall to form adhering portion so that the securing ends 6, 8 are stably located within the atrium. On the other hand, in the example illustrated in FIG. 5(a), both ends of the first securing end 6 and the second securing end 8 are respectively connected to mating both ends by means of supporting rods 12. This supporting rod 12 is an arbitrary element, and is not necessarily required to exist. It is preferable that the supporting rod has rigidity and malleability. The spacing between these two securing ends 6, 8 is kept constant (or, these two securing ends 6, 8 are maintained so as to provide an arrangement having a predetermined spacing or more) by means of the supporting rod 12.

Figure 6:
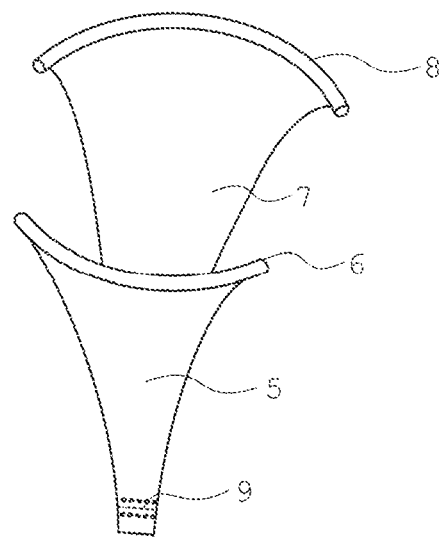
FIG. 6 is a conceptual diagram illustrating an example of an artificial heart valve according to the present invention having a securing end.

FIG. 6 is a conceptual diagram illustrating an example of an artificial heart valve according to the present invention having a securing end. For example, also when the artificial heart valve is the artificial tricuspid valve, in a manner similar to the artificial heart valve illustrated in FIG. 4, an artificial tricuspid valve may be inserted in a tricuspid valve direction from the right ventricular apex of the right ventricle and the valve leaflet securing portion 2 is opened in the state where the folded valve leaflet securing part 2 (the ring 3, or the securing ends 6, 8) is located within the right atrium to place the valve leaflet securing part 2 so that the valve leaflet securing part 2 continuously exist. Further, in this instance, the lower end of the artificial heart valve (artificial tricuspid valve) may be sutured to the right ventricular apex, or may be allowed to be drawn toward the outside of the heart from the right ventricular apex.

It is to be noted that, in connection with the artificial mitral valve, it is sufficient to move, as illustrated in FIG. 4, an artificial heart valve in the state where the valve leaflet securing portion 2 is folded to the left ventricle through the left atrium via the femoral vein, the jugular vein, the superior vena cava, or the inferior vena cava, and to guide it until a location in which the lower end of the artificial heart valve has been penetrated through the outside of the heart from within the left ventricle, the left ventricular apex of the left ventricle, or the left ventricular apex. Further, also in either case, in the state where the valve leaflet securing part is located within the left atrium, the valve leaflet securing part 2 is opened. Thus, the valve leaflet securing part 2 is disposed so that the valve leaflet securing part 2 continuously exists within the left atrium. In this way, the artificial mitral valve can be disposed, at a location to assist the function of the mitral valve, within the left ventricle and the left atrium. Further, the lower end of the artificial heart valve may be secured to the left ventricular apex by suturing the lower end of the artificial heart valve to the left ventricular apex, etc. By performing similar work also with respect to the artificial tricuspid valve, the artificial tricuspid valve can be disposed at a location to assist the function of the tricuspid valve (within the right ventricle and the right atrium).

Figure 7:
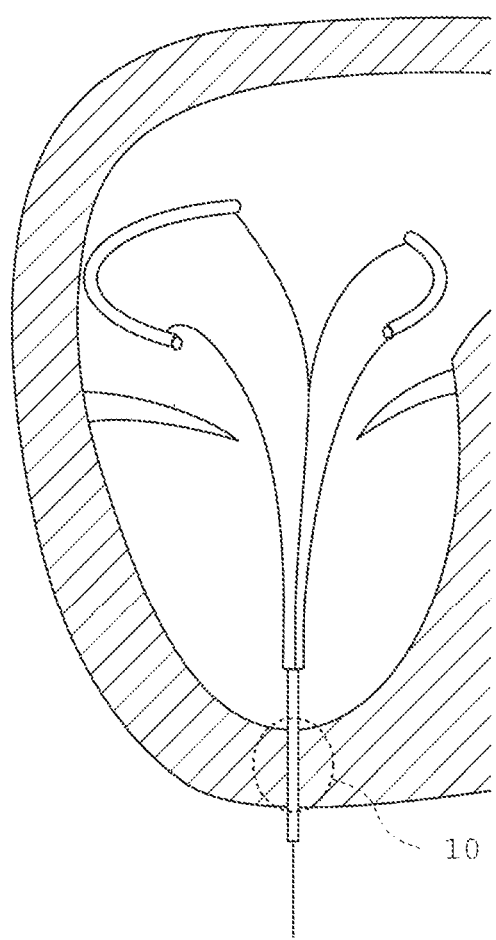
FIG. 7 is a conceptual diagram illustrating an artificial tricuspid valve (artificial valve assisting the function of the tricuspid valve).

FIG. 7 is a conceptual diagram illustrating an example in which the artificial heart valve according to the present invention having a securing part functions as an artificial tricuspid valve (an artificial valve to assist the function of the tricuspid valve). In this example, two securing ends are contained within the ventricle. Moreover, the lower end of the artificial tricuspid valve exists through the ventricular apex (may be secured to the ventricular apex later). Further, the portion with which the ventricular apex is in contact of the artificial tricuspid valve constitutes an apical junction.

Figure 8:
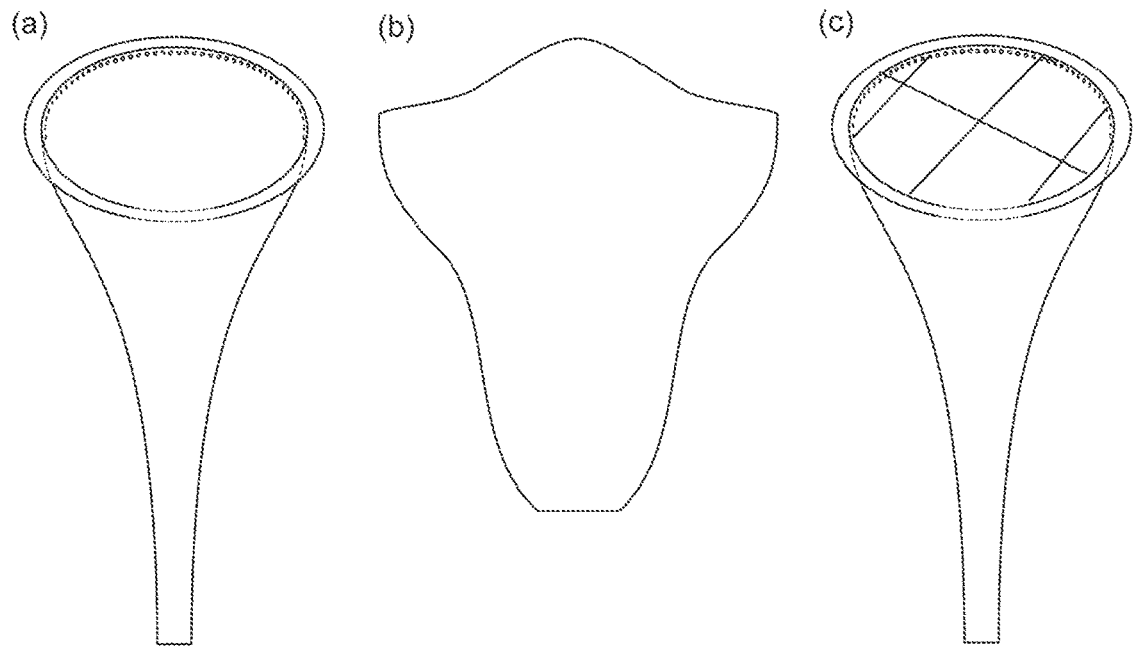
FIG. 8 is a conceptual diagram illustrating an example of an artificial heart valve comprised of a single valve leaflet.

An artificial heart valve comprised of a single valve leaflet 4 will now be described. The artificial heart valve comprised of a single valve leaflet 4 is fundamentally connected to the patient's own valve leaflet to thereby prevent blood regurgitation. Accordingly, it is preferable that this artificial heart valve may be connected to the patient's own valve leaflet. It is preferable that this heart valve is also connected (secured) to the ventricle by means of the ventricular apex anchoring portion. Thus, a situation such that the artificial heart valve moves toward the atrial side can be prevented. FIG. 8 is a conceptual diagram illustrating an example of an artificial heart valve comprised of a single heart valve leaflet. FIG. 8(a) illustrates an outside diagram of the artificial heart valve. FIG. 8(b) illustrates an outside diagram of the valve leaflet 4. FIG. 8(c) is a diagram illustrating an example of an artificial valve having supporting rods. The example illustrated in FIG. 8 is the artificial heart valve in which the number of valve leaflets 4 is one, and the valve leaflet securing part 2 is comprised of the ring. The ring and the valve leaflet have been already described. Nevertheless, preferred sizes of a valve leaflet when constituted with a single valve leaflet will be described on the basis of FIG. 1(b), they are given as below. A width W1 of upper end 21 which is a portion to be sewn to the ring 3 is, for example, 30 mm to 90 mm both inclusive. The width W1 may be 40 mm to 80 mm both inclusive, and may be 45 mm to 70 mm both inclusive. The valve leaflet is preferably such that when the circumference of the ring 3 is assumed as 100%, the portion of 15% to 45% both inclusive of the circumference of the ring is coated (or is connected at that portion), and may be such that the portion of 20% to 40% both inclusive is coated and may be such that the portion of 20% to 30% both inclusive is coated. The valve leaflet illustrated in FIG. 1(b) is such that a portion uniform in width exists at the upper part thereof. An example of the length (height) of this portion 25 is 1 mm to 10 mm both inclusive, and may be 2 mm to 8 mm both inclusive and may be 4 mm to 8 mm both inclusive. In this example, there exists a portion 27 which becomes narrower in width in a curved manner from the upper part which is constant in width toward the lower end 23 thereof. An example of the width of the lower end 23 is 2 mm to 20 mm both inclusive, and may be 3 mm to 10 mm both inclusive and may be 3 mm to 5 mm both inclusive. The height L1 of the valve leaflet is 20 mm to 70 mm both inclusive, and may be 25 mm to 65 mm both inclusive, may be 30 mm to 40 mm both inclusive, may be 40 mm to 70 mm both inclusive, and may be 40 mm to 60 mm both inclusive. Concrete sizes of the valve leaflet may be designed by taking into consideration, for example, the shape of the heart, the degree of blood regurgitation, and the state of disease of patients.

The artificial heart valve according to the present invention may be used in the treatment using the surgical operation in addition to the catheter approach (e.g., transapical approach and the transvenous approach). When the artificial heart valve is the mitral valve, either the catheter approach such as the transapical approach and the transvenous approach or the approach based on the surgical operation may be used. Also, when the artificial heart valve is the tricuspid valve, either the catheter approach such as the transapical approach and the transvenous approach or the approach based on the surgical operation may be used. The valve leaflet securing part 2 is secured to the valve leaflet 4 so that the valve leaflet 4 is continuously located above the heart valve (within the atrium). In addition, the valve leaflet securing part 2 may be connected to the atrial wall so that it is stably and continuously placed within the atrium.

Figure 9:
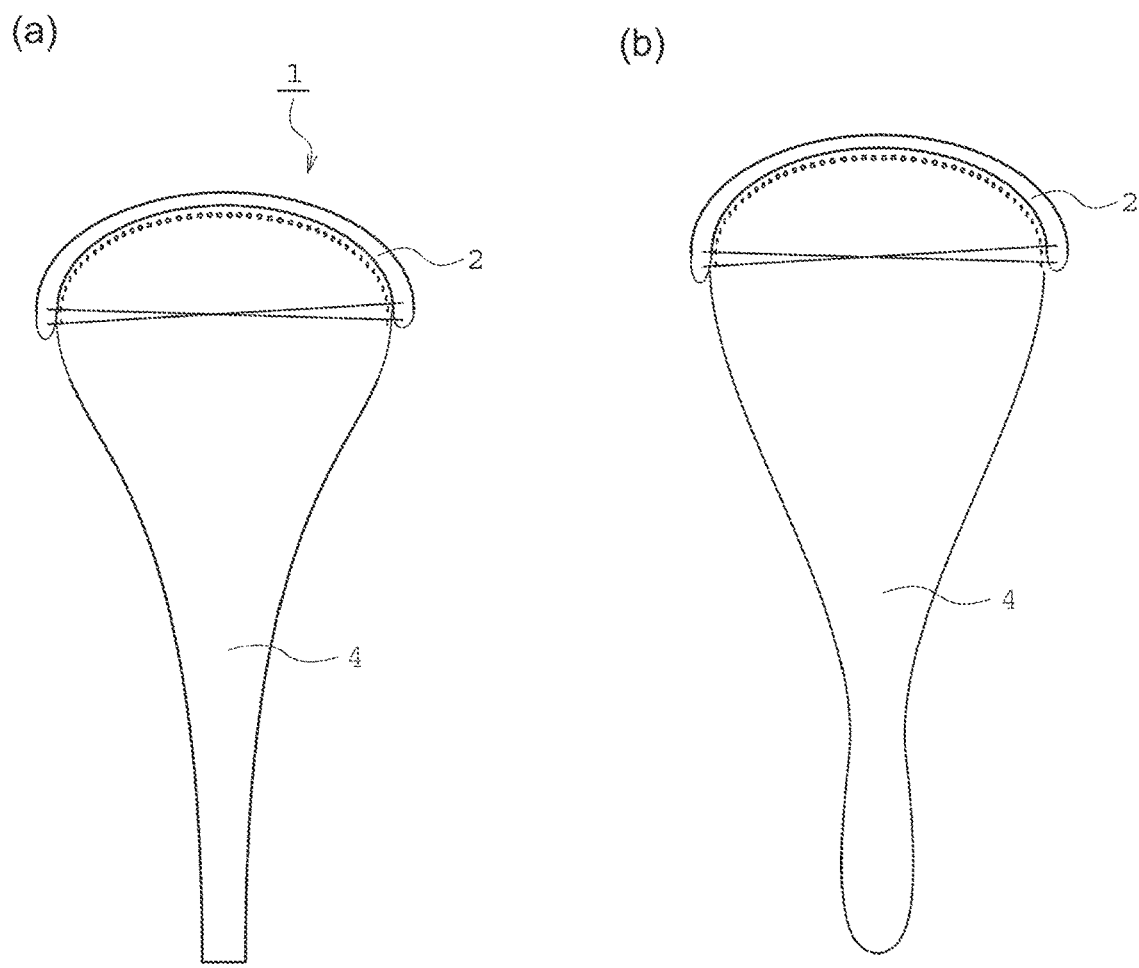
FIG. 9 is a conceptual diagram illustrating an example of an artificial heart valve comprised of a single valve leaflet.

FIG. 9 is a conceptual diagram illustrating an example of an artificial heart valve comprised of a single valve leaflet. In this example, the valve leaflet securing part 2 is formed with the securing end. For example, the length of the securing end may be allowed to be larger than that of the heart valve, thereby making it possible to prevent the heart valve from being moved toward the ventricular side. The securing end 6, 8 may be, e.g., curved rod-shaped securing end, or may be linearly elongated rod-shaped. Moreover, it is preferable that the securing end 6, 8 has a hardness higher than that of the valve leaflet 4. For the curved rod-shaped securing end, there may be employed a securing end comprising an arcuated rod-shaped portion, and a thread portion which connects to the rod-shaped tip. It is preferable that the securing end 6, 8 may be manufactured by biocompatible material. An example of the length of the securing end 6, 8 is 10 mm to 150 mm both inclusive. The length of the securing end 6, 8 may be 20 mm to 120 mm both inclusive, may be 40 mm to 100 mm both inclusive and may be 45 mm to 90 mm both inclusive. The thickness of the securing end 6, 8 may be 0.1 mm to 3 mm both inclusive, may be 0.3 mm to 2 mm both inclusive and may be 0.5 mm to 1 mm both inclusive.

The valve leaflet 4 illustrated in FIG. 9(*a*) may be fundamentally manufactured in a manner similar to the first valve leaflet 5 and the second valve leaflet 7 which have been described with reference to FIG. 1. As illustrated in FIG. 9(*b*), the valve leaflet has a shape capable of connecting to the artificial valve, and a shape which is formed to be broadest in width at the upper part of the artificial valve, smoothly becomes narrower in width until the middle thereof, smoothly becomes broader in width from a portion located below the artificial valve, and becomes narrower in the middle arriving at the lower end.

Figure 10:
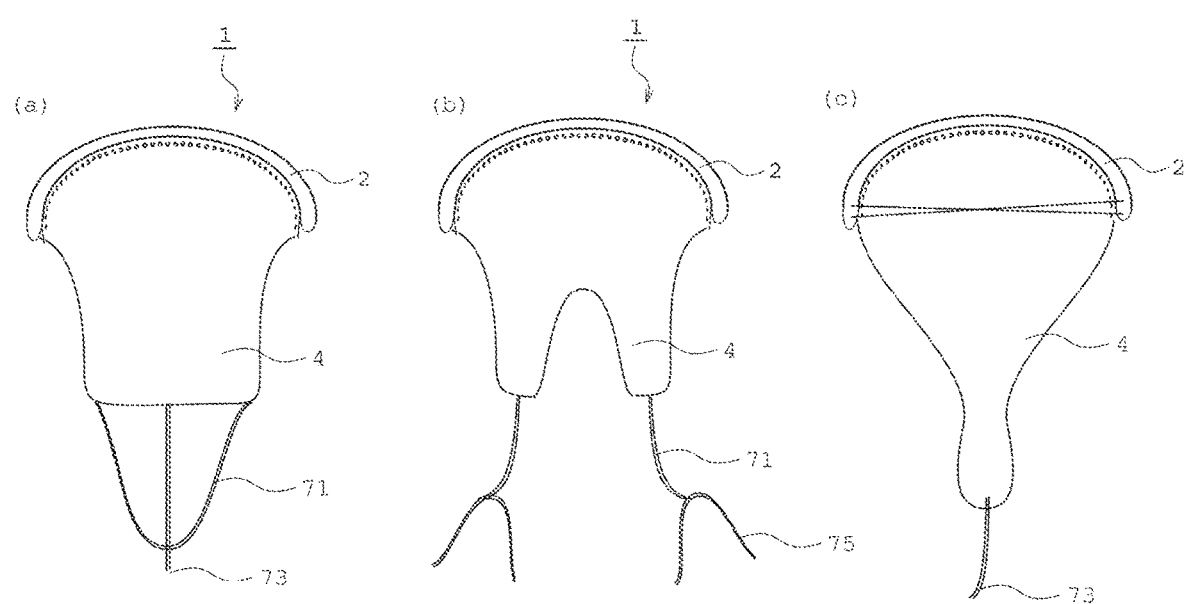
FIG. 10 is a conceptual diagram illustrating an example of an artificial heart valve having a thread like structure.

FIG. 10 is a conceptual diagram illustrating an example of an artificial heart valve having a thread-like structure. FIG. 10(*a*) is a conceptual diagram illustrating an example of the artificial heart valve comprising a thread like structure which connects portions in the vicinity of both left and right ends of the lower end of the valve leaflet, and an apical junction existing at the lower end of the thread like structure. FIG. 10(*b*) is a conceptual diagram illustrating an example of the artificial heart valve comprising a cutout from the portion in the vicinity of the central portion of the lower end of the valve leaflet toward the valve leaflet upper part, and respectively comprising thread like structures in the vicinity of both left and right ends of the lower end of the valve leaflet. FIG. 10(*c*) is a conceptual diagram illustrating an example of the artificial heart valve comprising an apical junction at the lower end of the valve leaflet. FIG. 10 depicts, as an example of the valve leaflet securing part 2, an artificial heart valve comprising securing end. However, there may be employed an artificial heart valve comprising a valve leaflet having a thread like structure, and a ring as the valve leaflet securing part 2. Moreover, FIG. 10 depicts a single valve leaflet. However, also in the artificial heart valve comprising two valve leaflets, any thread like structure may be provided similarly to FIG. 10. The thread like structure is, e.g., a portion narrow in width (e.g., 0.1 mm to 2 mm both inclusive, 0.5 mm to 1 mm both inclusive), which is attached to the valve leaflet. The thread like structure may be manufactured by resin such as PTFE or polypropylene, or may be manufactured by the same material as that of the valve leaflet. As long as there may be employed such an embodiment in which the thread like structure is connected to the valve leaflet, or is connected to an object where the valve leaflet is desired to be secured thus to ability to stabilize the valve leaflet or to regulate flow of blood, the number of threads and/or the shape thereof are not particularly limited.

FIG. 10(*a*) is a conceptual diagram illustrating an example of an artificial heart valve comprising a thread like structure 71 which connects portions in the vicinity of both left and right ends at the lower end of the valve leaflet, and an apical junction 73 existing at the lower end of the thread like structure. The apical junction 73 is connected to the apex of the heart. Thus, the artificial heart valve is stabilized. In this example, the thread like structure extends from the center of the lower part of the valve leaflet toward below the valve leaflet. Further, the thread like structure 71 which connects portions in the vicinity of both left and right ends of the lower end of the valve leaflet, and a thread like structure 71 extending from the center of the lower part of the valve leaflet toward below the valve leaflet are connected, and are connected to the apical junction 73. By allowing the valve leaflet near the apical junction 73 to be of the thread like structure, mobility of the valve port is enhanced so that the valve port area is increased.

FIG. 10(*b*) is a conceptual diagram illustrating an example of an artificial heart valve comprising a cutout from the portion in the vicinity of the center of the lower end of the valve leaflet 4 toward the valve leaflet upper part, and comprising thread like structures 71 respectively in the vicinity of both left and right ends of the lower end of the valve leaflet. At the tips of the thread like structures 71 of this artificial heart valve, securing parts 75 are respectively provided. These securing parts 75 are respectively connected to the ventricular wall or the papillary muscles. Thus, the valve leaflet will be connected to the ventricular wall or the papillary muscles through the thread like structures 71 so that the position of the artificial heart valve is stabilized. It is to be noted that securing parts 75 are directly provided at respective left and right portions of the lower end of the valve leaflet.

FIG. 10(*c*) is a conceptual diagram illustrating an example of an artificial heart valve comprising an apical junction at the lower end of the valve leaflet. In this example, a thread like structure extends from the lower end of the valve leaflet, and an apical junction 73 is provided at the tip thereof. Also, in this embodiment, a thread like structure 71 and a securing part 75 at the tip thereof may be provided on left and right side surfaces of the valve leaflet. When the securing part is connected to the thread like structure, a portion of the thread like structure may be tied with an object portion. Moreover, the securing part may be the thread like structure. In this case, for example, one end may be secured to the valve leaflet by means of thread, and the other end may be connected to the object portion (e.g., ventricular wall or papillary muscle).

INDUSTRIAL APPLICABILITY

The present invention can be utilized in the field of medical equipments.

DESCRIPTION OF REFERENCE NUMERALS

1 Artificial heart valve
3 Ring
5 First valve leaflet
7 Second valve leaflet
9 Lower part junction
13 Anchoring portion

The invention claimed is:

1. A method of assisting the function of a mitral valve or a tricuspid valve of a patient,
wherein the method comprises a step of providing an artificial heart valve (1) which assists the function of a mitral valve or a tricuspid valve, without removing the mitral valve or the tricuspid valve, in in the vicinity of mitral valve or in the vicinity of the tricuspid valve,
wherein the artificial heart valve (1) comprises a ring (3), a first valve leaflet (5), and a second valve leaflet (7),
wherein the first valve leaflet (5) and the second valve leaflet (7) are connected to the ring (3) at an upper part of the artificial heart valve (1),
wherein the first valve leaflet (5) and the second valve leaflet (7) are connected at a lower part junction (9) existing at a lower part of the artificial heart valve (1), and
wherein the first valve leaflet (5) and the second valve leaflet (7) have, at a lower part of the ring (3), a portion which become narrower in width toward the bottom thereof, and have a shape which is the narrowest in width at a lower end thereof,
wherein the artificial heart valve (1) further comprises an apical junction (10) at the lower part junction (9) or below the lower part junction (9) and the method further comprises a step of contacting the apical junction (10) with a ventricular apex of the patient.

2. A method according to claim 1,
wherein an upper part of the first valve leaflet (5) and an upper part of the second valve leaflet (7) are connected at an upper part junction (11).

3. A method according to claim 1,
wherein the first valve leaflet (5) or the second valve leaflet (7) is connected to a portion of the circumference of the ring (3), wherein the portion of the ring (3) is 30% to 99%, both inclusive, of the circumference of the ring (3).

4. A method according to claim 1,
wherein the ring (3) can be folded, and can be opened within the left atrium or the right atrium,
wherein the step of providing an artificial heart valve (1) comprises a step of opening the ring in a folded status within the left atrium or the right atrium.

5. A method according to claim 1,
wherein the ring has an annular shape having a diameter of 30 mm to 60 mm, both inclusive.

6. A method according to claim 1,
wherein either one of the ring (3), the first valve leaflet (5) and the second valve leaflet (7) comprise a anchoring portion (13) for anchoring it to a left atrial wall or a right atrial wall,
wherein the step of providing an artificial heart valve (1) comprises a step of anchoring the anchoring portion (13) to the left atrial wall or the right atrial wall.

7. A method according to claim 6,
wherein the anchoring portion (13) is an adhering portion or portions to a left atrial wall or a right atrial wall, which is or are provided at either one of the first valve leaflet (5) and the second valve leaflet (7) or at the both valve leaflets.

8. A method of assisting the function of a mitral valve or a tricuspid valve of a patient,
wherein the method comprises a step of providing an artificial heart valve (1) which assists the function of a mitral valve or a tricuspid valve, without removing the mitral valve or the tricuspid valve, in in the vicinity of mitral valve or in the vicinity of the tricuspid valve,
wherein the artificial heart valve (1) comprises a valve leaflet securing portion (2), and at least one valve leaflet (4),
wherein the valve leaflet (4) is connected to the valve securing part (2) at an upper part of the artificial heart valve (1),
wherein the valve leaflet (4) has a part (47) which becomes narrower in width toward the bottom thereof, and
wherein the artificial heart valve is an artificial mitral valve or an artificial tricuspid valve,
wherein the artificial heart valve (1) further comprises:
(A) a thread like structure (71) which is connected to portions in vicinity of both left and right ends at lower end of the valve leaflet (4), and
an apical junction (73) which exists at lower end of the thread like structure (71), wherein the apical 20 junction (73) is connectable to an apex of a heart; or
(B) the valve leaflet (4) comprises a cutout from a portion in vicinity of center of lower end of the valve leaflet (4) toward upper part of the valve leaflet (4), the artificial heart valve further comprises:
a first thread like structure (71) which is connected to a portion in vicinity of left end of lower end of the valve leaflet (4),
a second thread like structure (71) which is connected to a portion in vicinity of right end of lower 30 end of the valve leaflet (4),
a first securing part (75) which is connected to a tip of the first thread like structure (71) and is connectable to ventricular wall or papillary muscles, and
a second securing part (75) which is connected to a tip of the second thread like structure (71) and is connectable to ventricular wall or papillary muscles.

9. A method according to claim 8,
wherein the valve leaflet securing portion (2) is
(i) a ring (3), or
(ii) a securing end (6,8) attached to the valve leaflet (4).

10. A method according to claim 8,
wherein the valve leaflet securing part (2) is provided with means for preventing the artificial mitral valve or the artificial tricuspid valve from passing therethrough.

11. A method according to claim 8,
comprising an apical junction (10) in contact with a ventricular apex at the lower part junction (9) or below the lower part junction (9).

12. A method according to claim 8,
wherein the valve leaflet securing part (2) is
(i) a ring (3), or
(ii) a first securing end (6) and a second securing end (8) which are respectively attached to an upper part of the first valve leaflet (5) and an upper part of the second valve leaflet (7).

13. A method according to claim 8,
wherein either one of the valve leaflet securing part (2), the first valve leaflet (5) and the second valve leaflet (7) comprises an anchoring portion (13) for anchoring it to an atrial wall or an atrioventricular valve annulus,
wherein the step of providing an artificial heart valve (1) comprises a step of anchoring the anchoring portion (13) to the left atrial wall or the right atrial wall.

14. A method according to claim 13,
wherein the anchoring portion (13) is an adhering portion to the atrial wall or the atrioventricular valve annulus, which is or are provided at either one of the first valve leaflet (5) and the second valve leaflet (7) or at the both valve leaflets.

15. A method according to claim 8,
further comprising, in either valve leaflet, a securing part (75) for connecting the valve leaflet with a ventricular wall or a papillary muscle,
wherein the step of providing an artificial heart valve (1) comprises a step of connecting the valve leaflet with a ventricular wall or a papillary muscle by means of the securing part (75).

16. A method according to claim 8,
further comprising, in either valve leaflet, a securing part (75) for connecting the valve leaflet with a ventricular wall or a papillary muscle,
wherein the step of providing an artificial heart valve (1) comprises a step of connecting the valve leaflet with a ventricular wall or a papillary muscle by means of the securing part (75).

17. A method according to claim 8,
wherein the artificial heart valve (1) comprises:
(B) the valve leaflet (4) comprises a cutout from a portion in vicinity of center of lower end of the valve leaflet (4) toward upper part of the valve leaflet (4), the artificial heart valve further comprises:
a first thread like structure (71) which is connected to a portion in vicinity of left end of lower end of the valve leaflet (4),
a second thread like structure (71) which is connected to a portion in vicinity of right end of lower 30 end of the valve leaflet (4),
a first securing part (75) which is connected to a tip of the first thread like structure (71) and is connectable to ventricular wall or papillary muscles, and
a second securing part (75) which is connected to a tip of the second thread like structure (71) and is connectable to ventricular wall or papillary muscles.

18. A method of assisting the function of a mitral valve or a tricuspid valve of a patient,
wherein the method comprises a step of providing an artificial heart valve (1) which assists the function of a mitral valve or a tricuspid valve, without removing the mitral valve or the tricuspid valve, in in the vicinity of mitral valve or in the vicinity of the tricuspid valve,
wherein the artificial heart valve (1) comprises a valve leaflet securing portion (2), and at least one valve leaflet (4),
wherein the valve leaflet (4) is connected to the valve securing part (2) at an upper part of the artificial heart valve (1),
wherein the valve leaflet (4) has a part (47) which becomes narrower in width toward the bottom thereof, and
wherein the artificial heart valve is an artificial mitral valve or an artificial tricuspid valve,
wherein the artificial heart valve (1) further comprises:
a thread like structure which extends from lower end of the valve leaflet (4), and
an apical junction (73) which is provided at a tip of the thread like structure (71), wherein the apical junction (73) is connectable to an apex of a heart;
a first thread like structure (71) which is connected to a left side surface of the valve leaflet (4),
a second thread like structure (71) which is connected to a right side surface of the valve leaflet (4),
a first securing part (75) which is connected to a tip of the first thread like structure (71) and is connectable to ventricular wall or papillary muscles, and
a second securing part (75) which is connected to a tip of the second thread like structure (71) and is connectable to ventricular wall or papillary muscles.

* * * * *